United States Patent
Fettig et al.

(10) Patent No.: US 7,853,429 B2
(45) Date of Patent: Dec. 14, 2010

(54) CURVATURE-BASED EDGE BUMP QUANTIFICATION

(75) Inventors: Rabi Fettig, Somerville, MA (US); Jaydeep Kumar Sinha, Mansfield, MA (US)

(73) Assignee: KLA-Tencor Corporation, Milpitas, CA (US)

( * ) Notice: Subject to any disclaimer, the term of this patent is extended or adjusted under 35 U.S.C. 154(b) by 707 days.

(21) Appl. No.: 11/789,037

(22) Filed: Apr. 23, 2007

(65) Prior Publication Data

US 2008/0262751 A1    Oct. 23, 2008

(51) Int. Cl.
G01B 11/25 (2006.01)
G01B 11/24 (2006.01)
G06F 19/00 (2006.01)
G06F 17/40 (2006.01)

(52) U.S. Cl. .............. 702/167; 73/865.8; 356/237.5; 356/600; 382/145; 382/149; 702/81; 702/187; 702/189

(58) Field of Classification Search ............ 73/865.8; 356/237.1, 237.2, 237.3, 237.4, 237.5, 600, 356/625, 626, 630; 382/100, 108, 141, 145, 382/146, 147, 148, 149, 150; 438/14, 16; 702/1, 33, 35, 40, 81, 82, 83, 84, 127, 155, 702/159, 166, 167, 187, 189
See application file for complete search history.

(56) References Cited

U.S. PATENT DOCUMENTS

| | | | | |
|---|---|---|---|---|
| 2,798,966 A | * | 7/1957 | Summerhayes, Jr. | 250/559.08 |
| 3,136,069 A | * | 6/1964 | Reason | 33/554 |
| 3,615,143 A | * | 10/1971 | Reason et al. | 33/505 |
| 3,667,846 A | * | 6/1972 | Nater et al. | 356/623 |
| 4,109,508 A | * | 8/1978 | Fukuyama | 374/5 |
| 5,135,303 A | * | 8/1992 | Uto et al. | 356/237.2 |
| 5,463,464 A | * | 10/1995 | Ladewski | 356/601 |
| 5,465,153 A | * | 11/1995 | Ladewski | 356/601 |
| 5,973,777 A | * | 10/1999 | Nomoto et al. | 356/237.5 |
| 7,324,917 B2 | * | 1/2008 | Koliopoulos et al. | 702/155 |
| 2003/0023402 A1 | * | 1/2003 | Kobayashi et al. | 702/167 |
| 2006/0004542 A1 | * | 1/2006 | Koliopoulos et al. | 702/182 |
| 2008/0199978 A1 | * | 8/2008 | Fu et al. | 438/14 |

FOREIGN PATENT DOCUMENTS

WO    WO 2006/014317 A2 *    2/2006

OTHER PUBLICATIONS

SEMI M68-1108, 2007, 2008 (updated standard for Document No. 4209 of Semiconductor Equipment and Materials International, 3081 Zanker Road, San Jose, California 95134-2127, as referenced in the instant specification).

* cited by examiner

*Primary Examiner*—Edward R Cosimano
(74) *Attorney, Agent, or Firm*—Luedeka, Neely & Graham, P.C.

(57) ABSTRACT

Evaluating irregularities in surfaces of objects such as semiconductor wafers using a thickness profile of a surface section and analyzing the profile to obtain information of an irregularity start position, magnitude, and span along with surface slope and height information.

10 Claims, 8 Drawing Sheets

$$S_b(r) = \int_{BSR}^{r} C(\rho) d\rho$$

*FIG. 6*

$$h_b(r) = \int_{BSR}^{r} \int_{BSR}^{\gamma} C(\rho) d\rho d\gamma$$

CURVATURE-BASED EDGE BUMP QUANTIFICATION

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

The present invention relates to the measurement of surface topology of semiconductor wafers prior to their fabrication by semiconductor manufacturers into various micro circuits and other similar devices.

Semiconductor wafers are expensive real estate in that the manufacturers of semiconductor products need to know the quality of the surface area of the wafers, which can be as large as 300 cm across, before committing time, equipment and materials to process them into finished semiconductor products. If there is a sufficient perturbation in the surface profile of a portion of a semiconductor which could prevent its being processed into a finished product, that information needs to be known before the manufacturer proceeds so that that portion can be eliminated from processing. This problem is particularly severe in the edge areas of semiconductors where there tends to be a slope roll-off so that traditional thickness measurements by themselves are unlikely to reveal the presence of all or many bumps that affect the processing of finished semiconductor products.

Current processing and sensing techniques for a wafer surface profile are inadequate to accurately reveal the presence of a bump which exists as a significant variation from the local surface profile. Present techniques use a proximity probe which may, in fact, be a laser interferometer, to measure thickness of a wafer. This information is presently processed to provide a curvature profile by taking the second derivative of the curve representing data obtained by current probing technologies.

BRIEF SUMMARY OF THE INVENTION

The present invention aims at providing additional information about the bump (or depression anomaly) characteristics and in particular information about its start point radially from the semiconductor wafer central axis, the span of the bump to its maximum height and the actual height or departure from local surface level. That level is typically tilted with respect to a plane perpendicular to the wafer axis. Current semiconductor manufacturers need this additional information in order to accurately assess the suitability of all regions of a semiconductor wafer for processing purposes. The fact that a wafer may slope or roll off towards its edge does not necessarily disqualify it for purposes of producing finished semiconductor processes but a departure from the local plane of curvature could be a significant impediment.

The present invention provides additional signal processing which allows or provides the values of start point, peak point and distance therebetween which are essential to industry users. This data is obtained from the profile or second derivative curve by a process of integration of the profile value from the point where a rise in the local plane is first detected to outwardly extending radial points. A single integral will provide slope information about the wafer surface as a function of radius. The invention further provides for a double integral of the profile of curvature which will, in fact, provide surface normalized height information showing bumps and other perturbations above the local surface plane. Further, processing allows the maximum in the height information to be determined which can be used by manufacturers to judge the severity of the local departure from norm or bump.

BRIEF DESCRIPTION OF THE SEVERAL VIEWS OF THE DRAWINGS

These and other features of the present invention are illustrated in the figure, and accompanying detailed description wherein.

DETAILED DESCRIPTION OF THE INVENTION

Figure 1:
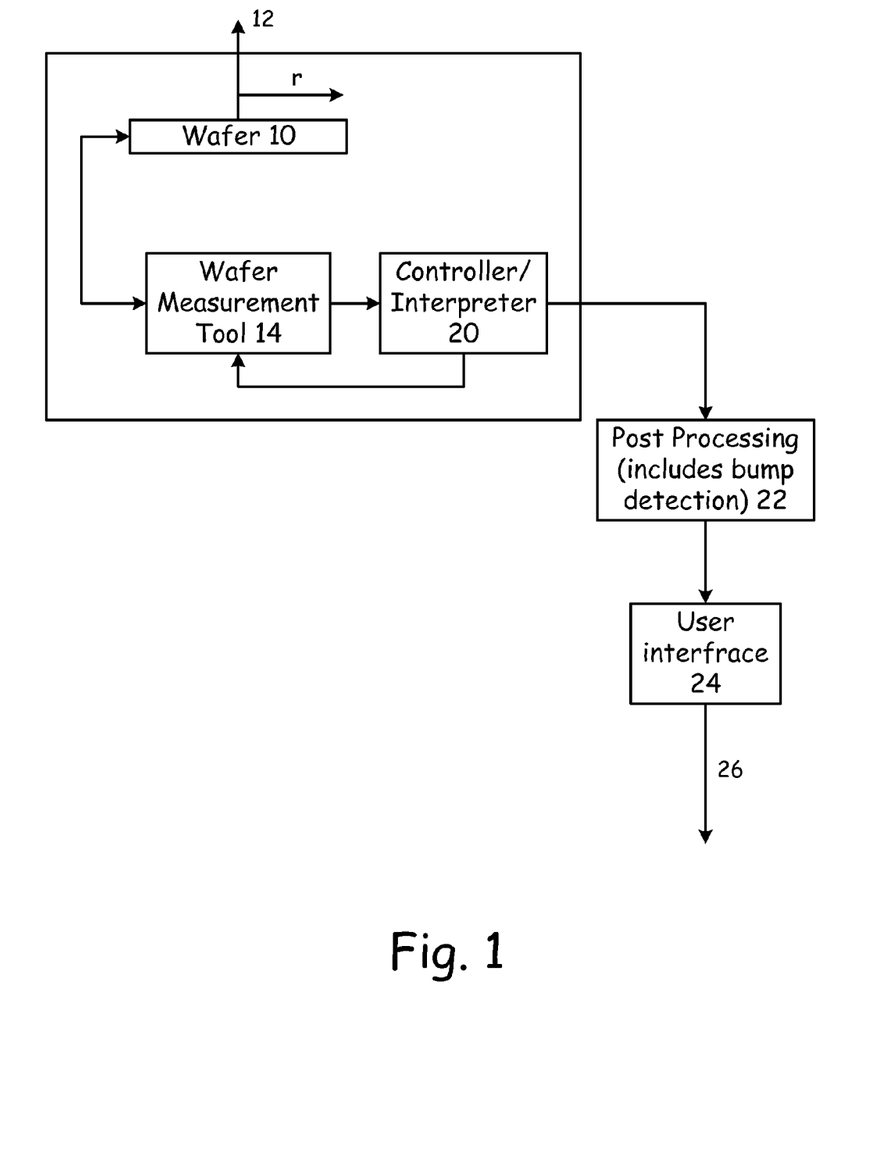
FIG. 1 illustrates a wafer surface condition evaluation system with which the invention is operative and which provides data reflecting profiles of the wafer front surface, back surface, or thickness.

As seen in FIG. 1, the present invention operates in the environment of testing of a semiconductor wafer 10 for surface characteristics which is typically accomplished by spinning the wafer about its center on an axis 12 with a sensor or wafer measurement tool 14 of a type known in the art to measure distance to the wafer 10. The sensor output is processed by a system 20 in conjunction with a microprocessor 22 to develop a profile, such as thickness or front/back surface distance, of the wafer 10 as it spins. Output information representing thickness or other parameters can be provided to a user interface 24 for use by I/O devices 26.

Figure 2:
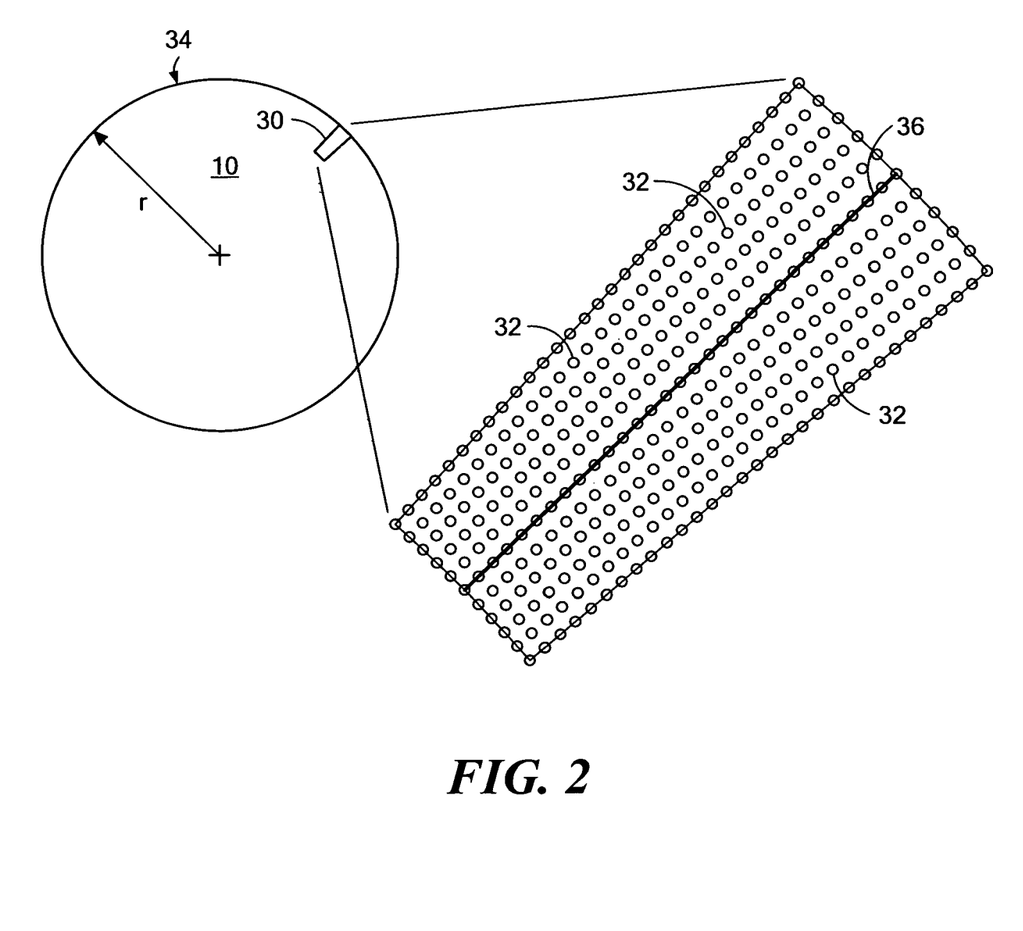
FIG. 2 illustrates data acquisition points on a semiconductor wafer surface as practiced in the invention.

In FIG. 2, a top view of the wafer 10 is shown illustrating part of typical processing of the thickness information provided by the sensor 14 and associated electronics. In particular, in a sector 30 the sensor head 14 makes a plurality of measurements 32, typically of thickness. The sector 30 may span a distance of 5° or more along the edge 34 of the wafer 10. The sector 30 typically includes data taken within that angle over a distance between and 1 and 5-10 mm from the edge 34. In typical application, the data in the segment 30 is averaged so as to provide thickness information along a radius vector 36. While the invention is particularly useful at an edge, it may also be used over the whole wafer or other parts thereof.

Figure 3:
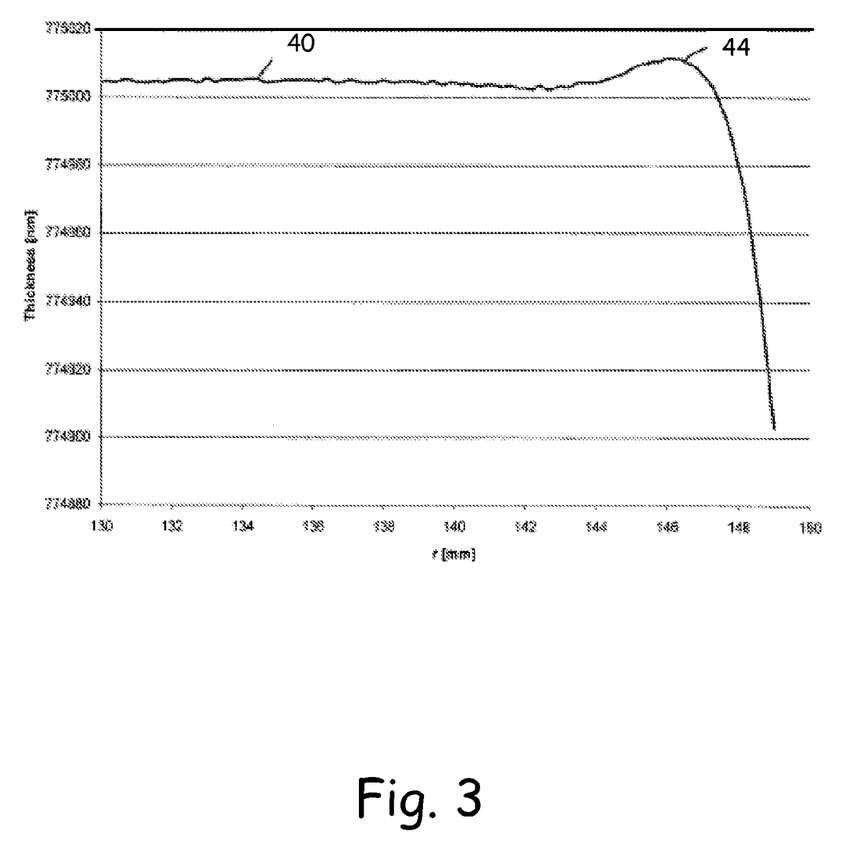
FIG. 3 illustrates a typical profile obtained from utilization of the measuring apparatus of FIG. 1.

Typical processing of information from the sensor 14, as described with respect to FIG. 2, will yield a profile curve 40 in FIG. 3, in this case a thickness profile. Such a profile 40 typically has a plurality of small surface unevenness. A larger anomaly would be classified as a bump 44, or possibly a void, or inverted bump. It is with information about such anomalies 44 that the invention is concerned. The profile 40 of thickness illustrates a gradual roll-off or reduction in thickness illustrated in FIG. 3, as the edge 34 of the wafer is reached.

Figure 4:
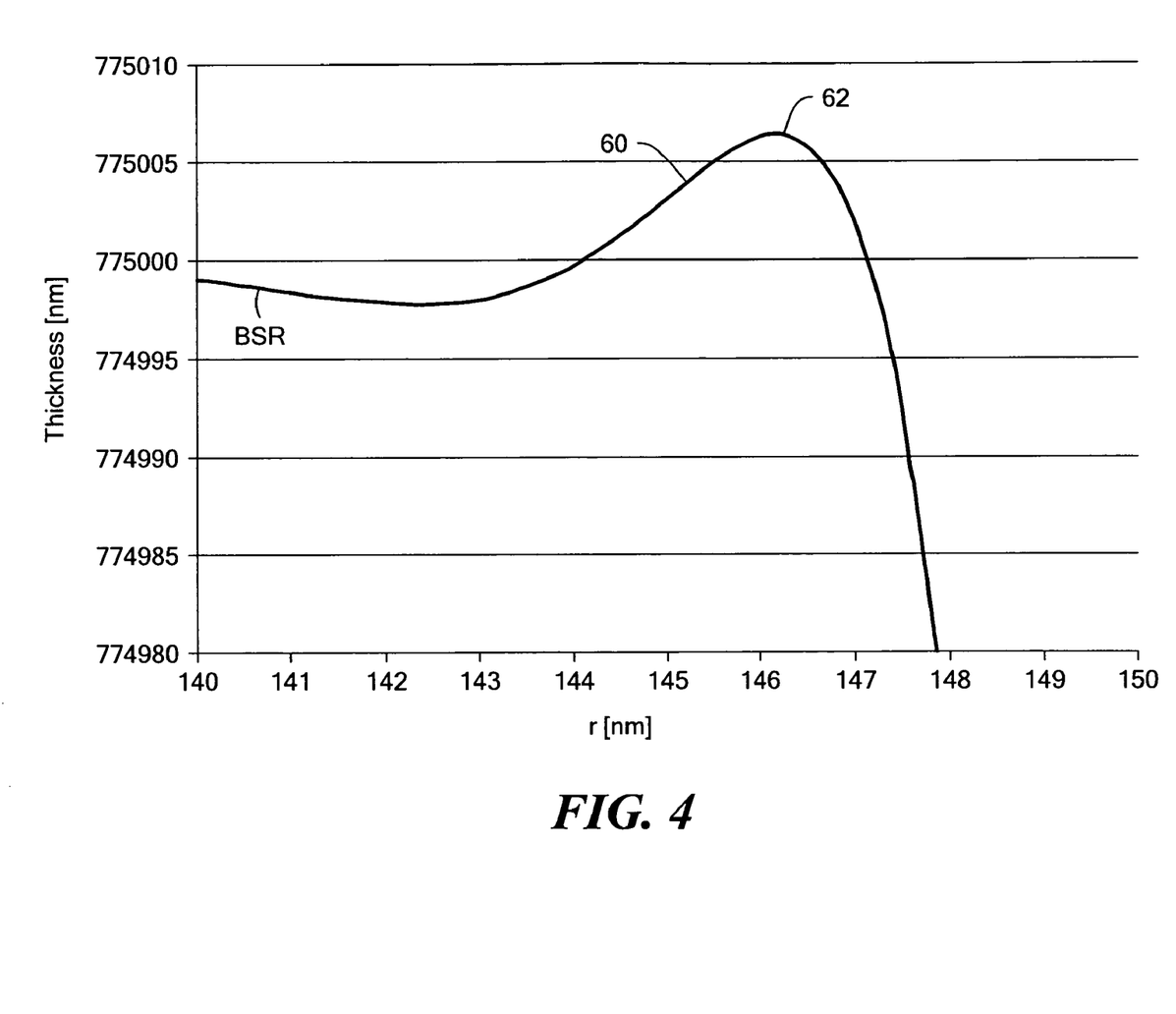
FIG. 4 illustrates a typical thickness profile.

FIG. 4 illustrates an expanded view of a thickness profile in the range of 140 to 150 mm from wafer center as a curve 60. When an anomaly 62 such as a bump is present, the change in the slope ($2^{nd}$ derivative) of curve 60 will go from negative to positive. This point marks a bump start radius (BSR). Second derivative processing converts the curve 60 of FIG. 4 to a ZDD profile 70 in FIG. 5. The profile 70 is typically referred to as the ZDD profile or metric. See Document No. 4209 of Semiconductor Equipment and Materials International, 3081 Zanker Road, San Jose, Calif. 95134-2127. That document bears a publication date of Nov. 6, 2006 and is incorporated herein by reference.

Figure 5:
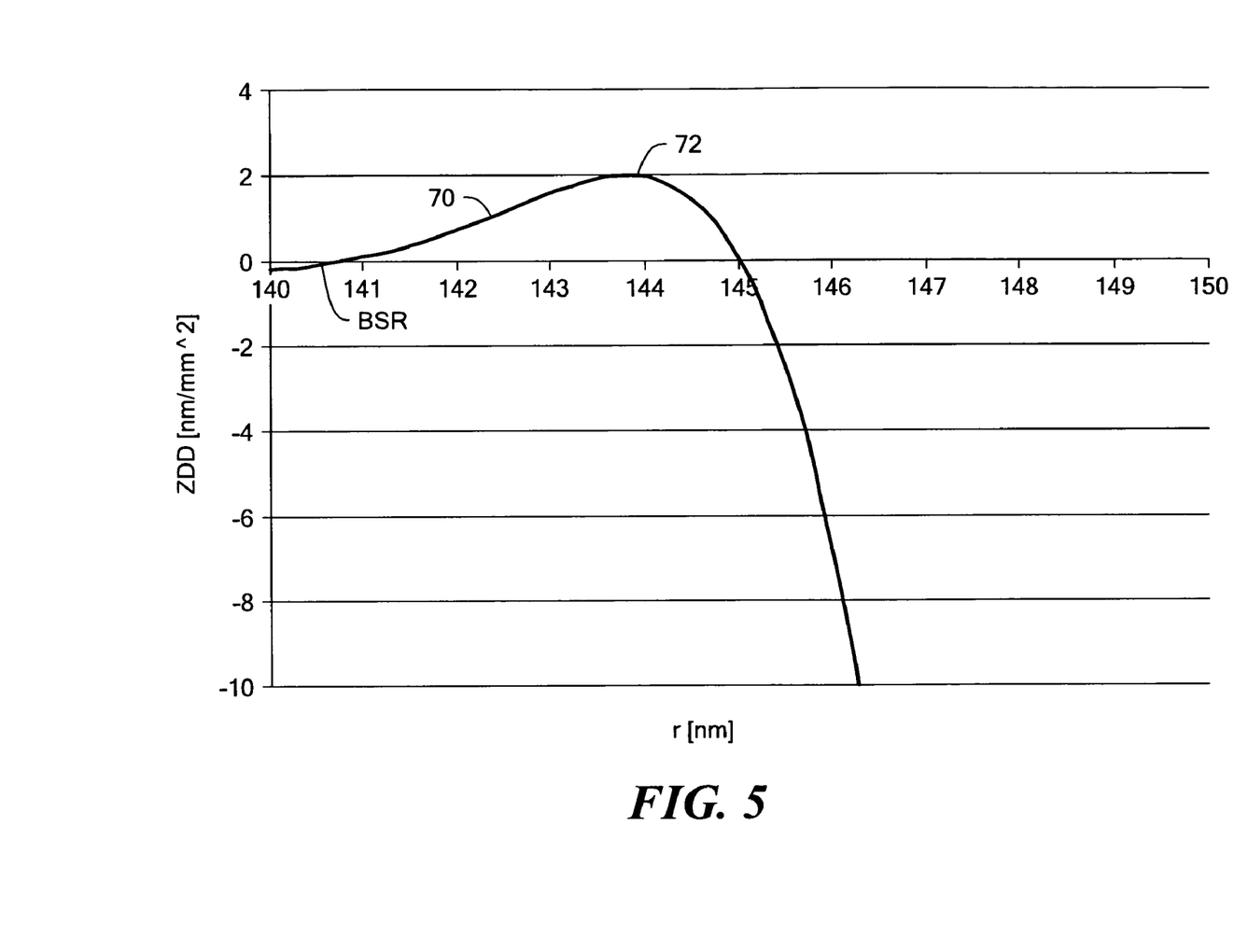
FIG. 5 illustrates a corresponding ZDD profile as practiced in the invention.

While both curves 60 and 70 illustrate the presence of respective bumps 62 and 72, the start position of the bump in FIG. 4 is rather indeterminate from mere thickness measurement given the roll-off nature of the wafer at its edge. In FIG. 5 however, because of the second derivative properties, the beginning of the bump (BSR), or void, is identifiable as the zero crossing in the profile curve, or second derivative curve, 70.

The demands of modern semiconductor processing and the cost of semiconductor real estate demands even better information about bumps or other anomalies be provided to the semiconductor manufacturer from testing of the raw semiconductor wafers. In order to accomplish that, the processing of FIGS. 6 and 7, typically by processor 22, which has provided the curve 70 of FIG. 5, is employed.

Figure 6:
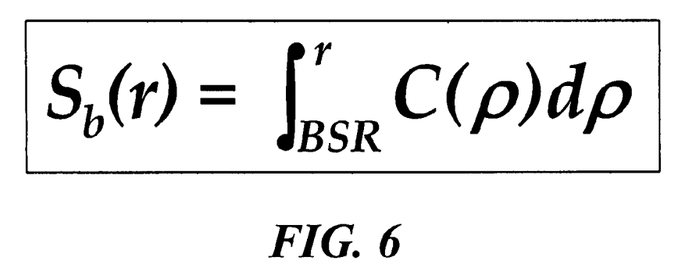
FIG. 6 illustrates processing of the data of FIG. 5 according to the present invention.
Figure 7:
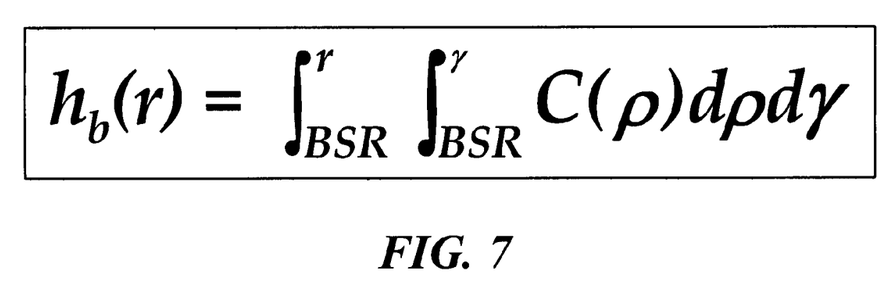
FIG. 7 illustrates further processing of the data of FIG. 5 according to the invention.

The processor 22 acts on the profile data of FIG. 5 to perform the integration of FIG. 6 in which r represents the radius as shown in FIG. 1 and is the variable of integration. The integration is from the bump start radius (BSR) out to the actual radius r. This provides a slope database. Height information is found using the integration of FIG. 7 in which a double integral is formed first from BSR to γ using the integration variable p followed by the integral from BSR to radius r using variable γ. The function C represents the curvature or ZDD profile 70 of FIG. 5. From the integration $h_b$, a function of radius r, the bump peak radius (BPR) is calculated as the radius of the peak value bump height, of the double integral. A void would be a minimum. The bump height is calculated as the peak value of the distance between that point and BSR is calculated as the radial span of the bump or anomaly. This information calculated by processor 22 provides the bump start point, the bump height and the radial distance between them, valuable information for the semiconductor manufacturers.

Figure 8:
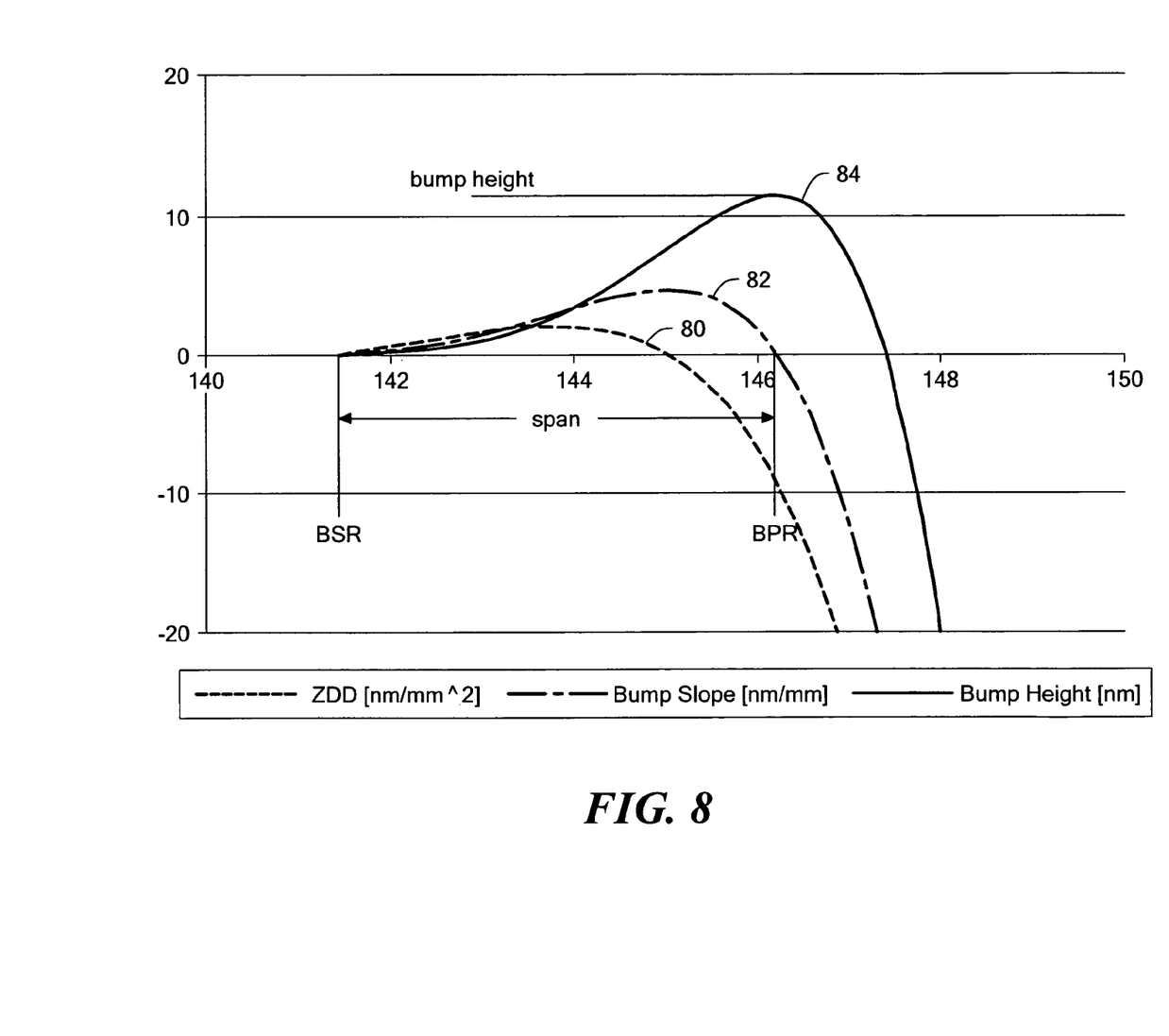
FIG. 8 illustrates graphically wafer anomaly data from processing according to the invention.

FIG. 8 illustrates these effects of the processing of the invention. A curve 80 corresponds to the profile 70 of FIG. 5. Curve 82 illustrates the results of the first integral processing of FIG. 6 to provide the slope $S_b$ information. The curve 84 illustrates the $h_b$ bump height information from the double integral of FIG. 7. This information clearly allows the calculation of the bump peak radius or maximum height (BPR) in curve 84. The span is the distance between BSR and BPR and the height is as given from the processor 22 evaluation of the maximum value of curve 84 using known technologies.

Figure 9:
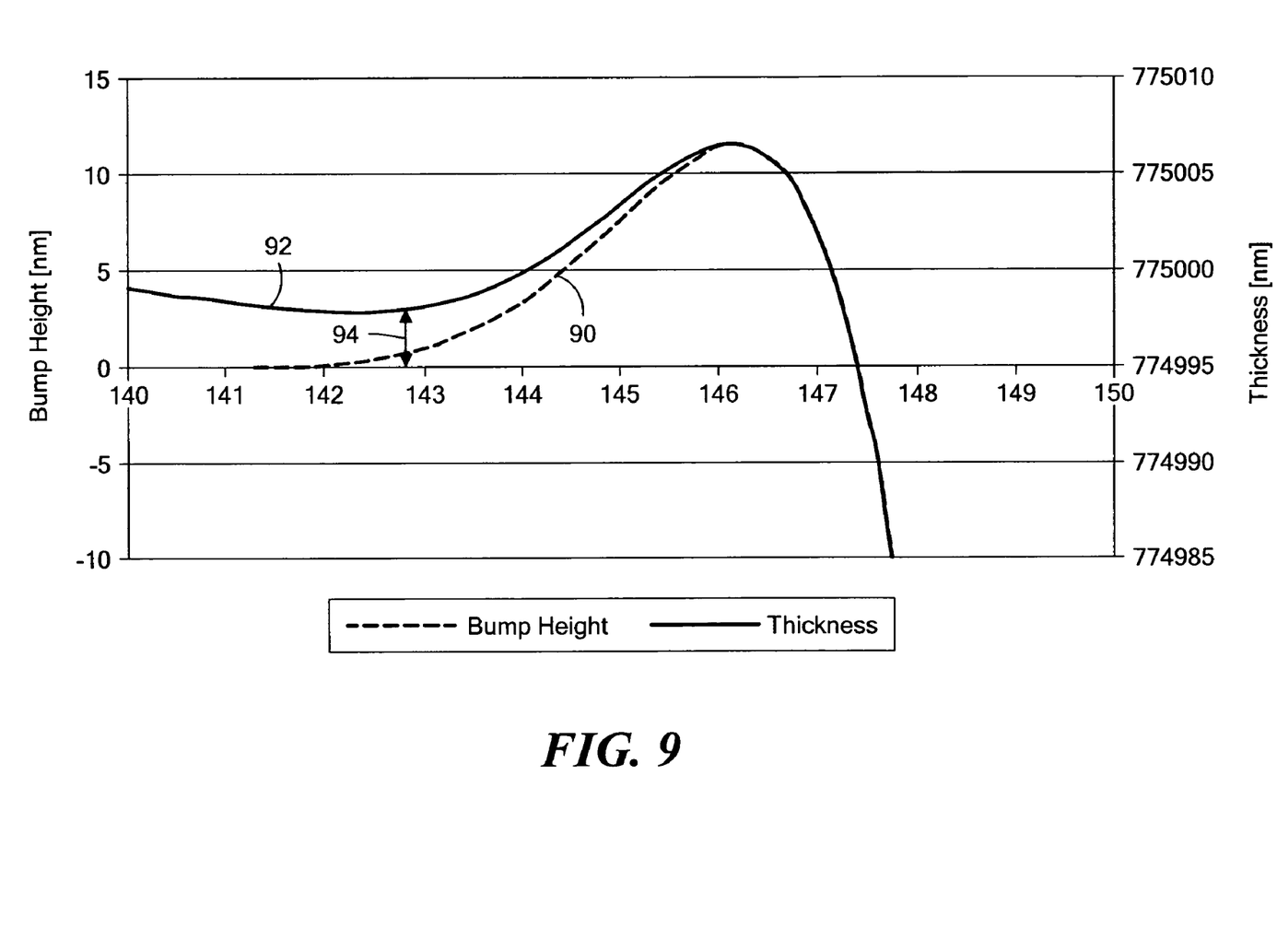
FIG. 9 illustrates the difference in detected surface anomalies between thickness data and anomaly measurements according to the invention.

The wafer tends to slope downward at the edges so that simple thickness information cannot readily be used to identify a variation in height relative to the near value of the slope throughout the edge region. This is illustrated in FIG. 9 which shows a gap 94 in minimum height between the thickness curve 90 and the bump height curve 92.

The above description is illustrative only and the inventions scope is provided by the following claims.

What is claimed is:

1. A wafer surface profile tool for characterizing an anomaly on the wafer, comprising:
   a wafer measurement tool for sensing height information within at least a sector at an edge of the wafer,
   a processor for,
      determining a shape profile for the wafer along at least a radial line within the sector, the shape profile comprising the sensed height information,
      processing the shape profile to produce a ZDD profile, representing a radial double derivative of the sensed height information,
      processing the ZDD profile to produce a slope profile,
      determining an anomaly span metric from the slope profile,
      processing the ZDD profile to produce a height profile, and
      determining an anomaly height metric from the height profile, and
   an output for providing at least the anomaly span metric and the anomaly height metric.

2. The wafer surface profile tool of claim 1, wherein the slope profile is produced from the ZDD profile by:

$$S_b(r) = \int_{BSR}^{r} C(\rho) d\rho$$

where
   $S_b(r)$ = the slope profile,
   r = radius of the wafer,
   $C(\rho)$ = the ZDD profile, and
   BSR = a bump start radius.

3. The wafer surface profile tool of claim 1, wherein the height profile is produced from the ZDD profile by:

$$h_b(r) = \int_{BSR}^{r} \int_{BSR}^{\gamma} C(\rho) d\rho d\gamma$$

where
   $S_b(r)$ = the slope profile,
   r = radius of the wafer,
   $C(\rho)$ = the ZDD profile, and
   BSR = a bump start radius.

4. The wafer surface profile tool of claim 1, wherein the anomaly is a bump.

5. The wafer surface profile tool of claim 1, wherein the anomaly is a recess.

6. A processor-based method for characterizing an anomaly on a wafer, the method comprising the steps of:
   receiving with the processor sensed height information within at least a sector at an edge of the wafer,
   determining with the processor a shape profile for the wafer along at least a radial line within the sector, the shape profile comprising the sensed height information,
   processing with the processor the shape profile to produce a ZDD profile, representing a radial double derivative of the sensed height information,
   processing with the processor the ZDD profile to produce a slope profile,
   determining with the processor an anomaly span metric from the slope profile,
   processing with the processor the ZDD profile to produce a height profile, and
   determining with the processor an anomaly height metric from the height profile, and using at least the anomaly span metric and the anomaly height metric to qualify the wafer for further processing.

7. The method of claim 6, wherein the slope profile is produced from the ZDD profile by:

$$S_b(r) = \int_{BSR}^{r} C(\rho) d\rho$$

where
  $S_b(r)$=the slope profile,
  r=radius of the wafer,
  $C(\rho)$=the ZDD profile, and
  BSR=a bump start radius.

8. The method of claim 6, wherein the height profile is produced from the ZDD profile by:

$$h_b(r) = \int_{BSR}^{r} \int_{BSR}^{\gamma} C(\rho) d\rho d\gamma$$

where
  $S_b(r)$=the slope profile,
  r=radius of the wafer,
  $C(\rho)$=the ZDD profile, and
  BSR=a bump start radius.

9. The method of claim 6, wherein the anomaly is a bump.
10. The method of claim 6, wherein the anomaly is a recess.

* * * * *